United States Patent
Brandt et al.

(10) Patent No.: US 11,253,447 B2
(45) Date of Patent: Feb. 22, 2022

(54) SPRAYABLE VOLUME POWDER FOR CREATING A SOFT HAIR FEEL

(71) Applicant: Henkel AG & Co. KGaA, Duesseldorf (DE)

(72) Inventors: Sandra Brandt, Pinneberg (DE); Anna Puls, Winsen (DE); Marcus Noll, Quickborn (DE); Diane Metten, Hamburg (DE)

(73) Assignee: HENKEL AG & CO. KGAA, Duesseldorf (DE)

( * ) Notice: Subject to any disclaimer, the term of this patent is extended or adjusted under 35 U.S.C. 154(b) by 0 days.

(21) Appl. No.: 16/669,255

(22) Filed: Oct. 30, 2019

(65) Prior Publication Data

US 2020/0170900 A1    Jun. 4, 2020

(30) Foreign Application Priority Data

Nov. 30, 2018 (DE) .................. 10 2018 130 538.9

(51) Int. Cl.
| | | |
|---|---|---|
| *A61K 8/25* | (2006.01) | |
| *A61K 8/895* | (2006.01) | |
| *A61Q 5/06* | (2006.01) | |
| *A61K 8/34* | (2006.01) | |
| *A61K 8/36* | (2006.01) | |

(52) U.S. Cl.
CPC ............... *A61K 8/25* (2013.01); *A61K 8/345* (2013.01); *A61K 8/36* (2013.01); *A61K 8/895* (2013.01); *A61Q 5/06* (2013.01)

(58) Field of Classification Search
None
See application file for complete search history.

(56) References Cited

U.S. PATENT DOCUMENTS

| | | | |
|---|---|---|---|
| 5,323,936 A | 6/1994 | Wolter et al. | |
| 9,415,001 B2 | 8/2016 | Masatomi et al. | |
| 2013/0302394 A1 | 11/2013 | Dumousseaux et al. | |
| 2014/0004065 A1* | 1/2014 | Souda ................ | A61K 8/89 424/59 |
| 2017/0172908 A1* | 6/2017 | Puls et al. ............ | A61K 8/4953 |
| 2017/0360682 A1* | 12/2017 | Debeaud ................ | A61K 8/31 |

FOREIGN PATENT DOCUMENTS

| | | |
|---|---|---|
| EP | 0473965 A1 | 3/1992 |
| EP | 0765656 A1 | 4/1997 |
| EP | 1481660 A1 | 12/2004 |
| EP | 2654669 A2 | 10/2013 |
| EP | 2841488 A1 | 3/2015 |
| WO | 2013117549 A2 | 8/2013 |
| WO | 2017197196 A1 | 11/2017 |

* cited by examiner

*Primary Examiner* — Quanglong N Truong
(74) *Attorney, Agent, or Firm* — Lorenz & Kopf, LLP

(57) ABSTRACT

The present disclosure relates to a cosmetic agent for the treatment of keratinic fibers, in particular human hair, wherein the cosmetic agent constitutes a powder containing hydrophobically modified silicon dioxide and particles comprising a silicone elastomer. Furthermore, the present disclosure relates to a spray applicator comprising the cosmetic agent. In addition, the present disclosure relates to the use of the cosmetic agent.

17 Claims, No Drawings

SPRAYABLE VOLUME POWDER FOR CREATING A SOFT HAIR FEEL

CROSS-REFERENCE TO RELATED APPLICATION

This application claims priority to German Patent Application No. 10 2018 130 538.9, filed Nov. 30, 2018, which is incorporated herein by reference in its entirety.

TECHNICAL FIELD

Powdered cosmetics are known in the prior art. These have long been used, for example, in the field of skin treatment. Typical examples are make-up powder or eye shadow. Furthermore, surfactant-free but solvent-containing dry shampoos which are sprayed onto the fibers by employing an aerosol device are used for hair treatment. The starch particles contained in the dry shampoo absorb sebum and dirt after evaporation of the solvent and are brushed off after a contact time. Furthermore, the person skilled in the art knows of powdered hair colors which, however, are not applied in powder form to the fibers but are previously stirred with separately added water to form a coloring cream. The resulting cream is then applied to the hair.

BACKGROUND

Styling agents for the deformation of keratinic fibers are generally known and are used in various embodiments to build, refresh and fix hairstyles with many hair types that can only be obtained using firming agents. In this case, both hair treatment agents, which are used for a permanent and a temporary shaping of the hair, play an important role. The temporary shapings, which are intended give a good hold without impairing the healthy appearance of the hair, such as its shine, can be achieved, for example, by hair sprays, hair waxes, hair gels, hair waves, etc.

Corresponding agents for temporary shaping usually contain synthetic polymers as the shaping component. Preparations containing a polymer can be applied to the hair by employing propellant gases or by a pumping mechanism. Hair gels and hair waxes, however, are usually not applied directly to the hair, but distributed by employing a comb, or they are massaged with the hands into the hair.

Known embodiments of temporary styling agents often cannot be dosed with satisfactory accuracy. Thus, hair gels, hair creams and hair waxes are difficult to distribute once they are applied to the hair. As soon as the comb or the hands to which the styling agent has been applied come into contact with the first portions of hair, comparatively large amounts of styling agent are delivered to the hair. Comparatively little styling agent is incorporated in hair portions which are only reached later with the comb or the hands. This has the consequence that the user either has to apply a large amount of styling agent from the beginning, so that even the last reached hair portions receive sufficient styling agent, or the user is forced to apply the styling agent in several steps, each treating other hair portions. Hair sprays can be distributed more evenly on the hair.

Furthermore, there are also volume powders, which are applied to the hair for volume and temporary deformability. Conventional volume powders usually constitute solid powders which can be removed from a container by a bulk process. The handling of the conventional powder is disadvantageous since dust is produced during the removal. Furthermore, powders are not easy to apply to longer hair and are associated with a detrimental haptic feel on the hand.

In addition to the handling of the cosmetic styling agents, the performance that can be achieved with the agent is also of great importance. Conventional cosmetic styling agents, in particular those to be used as volume powders, are very rough and leave a very dull feeling on the hair and during and after application to the palms. This in particular creates an unpleasant feeling with longer hair.

Furthermore, in addition to the subjective feeling of the user, the externally visible performance should also be at a high level. The requirements for cosmetic agents are generally very high. From volume powders, the user expects an externally visible effect on the desired texture produced by the agent and, of course, the volume produced is intended to provide a pleasing appearance of the hair.

BRIEF SUMMARY

Cosmetic agents for the treatment of keratinic fibers and spray applicators including the cosmetic agent are provided herein. In an embodiment, a cosmetic agent for the treatment of keratinic fibers is provided, where the cosmetic agent includes a powder. The powder includes hydrophobically modified silicon dioxide and particles including a silicone elastomer.

In another embodiment, a cosmetic agent for the treatment of keratinic fibers is provided. The cosmetic agent includes:
  from about 70 to about 80% by weight of water
  from about 7 to about 20% by weight of hydrophobically modified silicon dioxide that is a silylation product of a reaction of a precipitated silica and/or a fumed silica with an organosilicon compound;
  from about 7 to about 20% by weight of particles comprising a composite material, wherein the composite material consists of Dimethicone/Vinyldimethicone Crosspolymer and silicon dioxide;
  a divalent and/or trivalent carboxylic acid; and
  from about 2 to about 18% by weight of a water-soluble care agent selected from the group of ethylene glycol, 1,2-propylene glycol, 2-methyl-1,3-propanediol, glycerol, 1,2-butylene glycol, 1,3-butylene glycol, 1,4-butylene glycol, 1,2-pentanediol, 1,5-pentanediol;
  wherein the particles have an average particle size of from about 0.1 to about 20 μm.
  each based on the total weight of the cosmetic agent.

DETAILED DESCRIPTION

The following detailed description is merely exemplary in nature and is not intended to limit the disclosure or the application and uses of the subject matter as described herein. Furthermore, there is no intention to be bound by any theory presented in the preceding background or the following detailed description.

The object underlying the present disclosure is to overcome the above-mentioned disadvantages associated with conventional volume powders. The object underlying the present disclosure is to provide a volume powder, which provides an advantageous handling, which in particular produces a softer hair feeling and a softer feel in the hands during application. Furthermore, the present disclosure was based on the object of ensuring uniform applicability, especially for longer hair. In addition, the present disclosure has the object to improve the performance in terms of the volume achieved and the texture achieved in treated hair compared to conventional agents.

The object underlying the present disclosure is solved by a cosmetic agent as contemplated herein. A first subject of the present disclosure is therefore a cosmetic agent for the treatment of keratinic fibers, in particular human hair, the cosmetic agent constituting a powder containing hydrophobically modified silicon dioxide and particles comprising a silicone elastomer.

The cosmetic agent contains hydrophobically modified silicon dioxide as the first required component. This is precipitated silica or pyrogenically produced silicon dioxide, the particle surface of which has been chemically treated to be more hydrophobic than untreated silicon dioxide. The silicon dioxide should in any case be wholly or predominantly amorphous.

The cosmetic agent contains a substance comprising a silicone elastomer as a second required component. In the context of the present disclosure, a silicone elastomer is to be understood to mean an elastomer which comprises organopolysiloxanes which are at least partially crosslinked. Expressed otherwise, silicone elastomers are materials that can be converted into the rubber-elastic state, which materials contain polyorganosiloxanes which have groups accessible for crosslinking reactions. As such, hydrogen atoms, hydroxy groups and vinyl groups can be considered, which can be located at the chain ends, but can also be incorporated into the polymeric chain of polyorganosiloxanes.

Cosmetic agents comprising the two components provide sprayable powders suitable for hair treatment. In the context of the present disclosure, a hair treatment is understood to mean hair care, shaping, in particular temporary shaping, volume generation and/or styling of a hairstyle.

The term "particles comprising a silicone elastomer" in the context of the present disclosure is intended to mean that the material comprising the silicone elastomer is particulate in the cosmetic agent. Particulate silicone elastomers offer the advantage of causing a pleasant skin feel after the liquid component of the cosmetic agent dries.

According to a preferred embodiment of the present disclosure, the silicone elastomer is a crosslinked polyorganosiloxane selected from the group of a crosslinked polydimethylsiloxane, a crosslinked polydimethylsiloxane/methylvinylsiloxane, a crosslinked polydimethylsiloxane/diphenylsiloxane, a crosslinked polydimethylsiloxane/phenylmethylsiloxane, a crosslinked polydimethylsiloxane/diphenylsiloxane/methylvinylsiloxane, a polydimethylsiloxane gum and a crosslinked Dimethiconol (INCI). A crosslinked polydimethylsiloxane is to be understood to mean a Dimethicone (INCI) which contains any crosslinkable groups which have been completely or partially reacted for crosslinking. The same applies to the other polyorganosiloxanes which contain no obviously recognizable crosslinkable groups. For example, in the polydimethylsiloxane/diphenylsiloxane/methylvinylsiloxane, the vinyl group, as recognized by those skilled in the art, constitutes a crosslinkable group.

It has been found to be particularly preferred when the particles comprising the silicone elastomer constitute a composite material, wherein the composite material comprises a crosslinked polyorganosiloxane and silicon dioxide. More preferably, the composite material comprises a crosslinked polyorganosiloxane on silicon dioxide, that is, the silicon dioxide is bonded at its surface to the polyorganosiloxane. More preferably, the composite material comprises the Dimethicone/Vinyldimethicone Crosspolymer (INCI) on silicon dioxide, and most preferably, the composite material consists substantially of Dimethicone/Vinyldimethicone Crosspolymer (INCI) and silicon dioxide. The Dimethicone/Vinyldimethicone Crosspolymer is commercially available, for example, under the name Dow Corning 9701 from Dow.

In the context of the present disclosure, a composite material is to be understood to mean a material which consists of at least two different materials which are bound one another, wherein the properties of the material in a bound form differ from the properties of the individual materials which are present separately from one another. The feature according to which the crosslinked polyorganosiloxane is "on" silicon dioxide is to be understood to mean that the crosslinked polyorganosiloxane is wholly or partially coated on the surface of silicon dioxide particles.

The hydrophobically modified silicon dioxide is necessarily different from the composite material comprising the silicone elastomer and silicon dioxide.

It has surprisingly been found that the use of the two constituents containing the hydrophobically modified silicon dioxide as a first component and the described composite material comprising a silicone elastomer and silicon dioxide as a second component has the advantages that in particular long hair can be textured more easily, that the cosmetic agent comprising the two components provides a good volume of hair, that the treated hair and hands feel good during incorporation and that the cosmetic agent can be better handled by employing a spraying process due to the better applicability. The effect of the rough tips does not appear for longer hair.

Keratinic fibers, in the context of the present disclosure, are understood to mean furs, wool, feathers and, in particular, human hair.

According to a preferred embodiment, the particles have an average particle size of from about 0.1 to about 20 µm, preferably from about 0.5 to about 15 µm, more preferably from about 0.9 to about 12 µm, and most preferably from about 1 to about 10 µm. In particular, the composite material has an average particle size of from about 0.1 to about 20 µm, preferably from about 0.5 to about 15 µm, more preferably from about 0.9 to about 12 µm, and most preferably from about 1 to about 10 µm. The average particle size is to be measured by employing a microscope by observing particles in the projection, determining the smallest diameter and the largest diameter of a particle and calculating the mean value therefrom. This mean value is determined for a sufficient number of particles, and then the arithmetic mean is determined from the several mean values.

The average particle sizes above have the advantage of not being too low. Particles that are too small tend to aggregate. Furthermore, the particles are not so large that they would be visible after an application to the hair.

According to a preferred embodiment of the present disclosure, the cosmetic agent contains an organic acid, preferably a divalent and/or trivalent organic acid, more preferably a divalent and/or trivalent carboxylic acid, most preferably citric acid. The term divalent or trivalent acid or carboxylic acid is understood by the person skilled in the art to mean that each acid molecule has two or three acid functions.

According to a preferred embodiment of the present disclosure, the hydrophobically modified silicon dioxide is a silylation product of a reaction of a precipitated silica and/or a fumed silica with an organosilicon compound, the organosilicon compound preferably being an alkylsiloxane, a silane, preferably trimethylsilane, or a silazane, more preferably the organosilicon compound being an alkylsilazane, in particular hexamethyldisilazane.

The hydrophobically modified silicon dioxide is a superficially hydrophobized silicon dioxide. The hydrophobically modified silicon dioxide is known and can be obtained under the generic term silica silylate from various manufacturers, for example, under the product name Aerosil R 812 S.

According to a further preferred embodiment, the cosmetic agent contains from about 50 to about 90% by weight, preferably from about 60 to about 95% by weight, more preferably from about 70 to about 80% by weight of water, from about 5 to about 30% by weight, preferably from about 6 to about 25% by weight, more preferably from about 7 to about 20% by weight of hydrophobically modified silicon dioxide, and from about 2 to about 30% by weight, preferably from about 5 to about 25% by weight, more preferably from about 7 to about 20% by weight of particles comprising the silicone elastomer, in each case based on the total weight of the cosmetic agent. Advantageous effects with regard to handling and performance in hair styling can be achieved within these limits.

According to a further preferred embodiment of the present disclosure, the cosmetic agent comprises a water-soluble care agent, which is preferably a polyvalent alcohol which is more preferably selected from the group of ethylene glycol, 1,2-propylene glycol, 2-methyl-1,3-propanediol, glycerol, 1,2-butylene glycol, 1,3-butylene glycol, 1,4-butylene glycol, 1,2-pentanediol, 1,5-pentanediol, in particular glycerol. Particularly preferably, the cosmetic agent further contains a water-soluble care agent, in particular glycerol, in an amount of from about 2 to about 18% by weight, preferably from about 5 to about 15% by weight, more preferably from about 8 to about 12% by weight, based on the total weight of the cosmetic agent.

The applicability of the cosmetic agent can also be further increased by the use of small amounts of one or more polyvalent alcohols. The preferred diols or glycerol improve the applicability and are nourishing.

In further preferred embodiments of the present disclosure, the cosmetic agent further contains preservatives, perfume and optionally further excipients.

Very particularly preferred cosmetic agents as contemplated herein comprise at least one of the following embodiments A) to J):

A)
Cosmetic agent for treating keratinic fibers, in particular human hair, wherein the cosmetic agent constitutes a powder comprising hydrophobically modified silicon dioxide and particles comprising a composite material, wherein the composite material comprises a crosslinked polyorganosiloxane and silicon dioxide.

B)
Cosmetic agent for treating keratinic fibers, in particular human hair, wherein the cosmetic agent constitutes a powder comprising hydrophobically modified silicon dioxide and particles comprising a composite material, wherein the composite material comprises a crosslinked polyorganosiloxane on silicon dioxide.

C)
Cosmetic agent for treating keratinic fibers, in particular human hair, wherein the cosmetic agent constitutes a powder comprising hydrophobically modified silicon dioxide and particles comprising a composite material, wherein the composite material comprises Dimethicone/Vinyldimethicone Crosspolymer (INCI) on silicon dioxide.

D)
Cosmetic agent for treating keratinic fibers, in particular human hair, wherein the cosmetic agent constitutes a powder comprising hydrophobically modified silicon dioxide and particles comprising a composite material, wherein the composite material consists of Dimethicone/Vinyldimethicone Crosspolymer (INCI) and silicon dioxide.

E)
Cosmetic agent for treating keratinic fibers, in particular human hair, wherein the cosmetic agent constitutes a powder comprising hydrophobically modified silicon dioxide and particles comprising a composite material, wherein the composite material comprises a crosslinked polyorganosiloxane on silicon dioxide, and the particles have an average particle size of from about 0.1 to about 20 µm, preferably from about 0.5 to about 15 µm, more preferably from about 0.9 to about 12 µm and most preferably from about 1 to about 10 µm.

F)
Cosmetic agent for treating keratinic fibers, in particular human hair, wherein the cosmetic agent constitutes a powder comprising hydrophobically modified silicon dioxide and particles comprising a composite material, wherein the composite material comprises a crosslinked polyorganosiloxane on silicon dioxide, and wherein the cosmetic agent contains a divalent and/or or trivalent carboxylic acid, preferably citric acid.

G)
Cosmetic agent for treating keratinic fibers, in particular human hair, wherein the cosmetic agent constitutes a powder comprising hydrophobically modified silicon dioxide and particles comprising a composite material, wherein the composite material comprises a crosslinked polyorganosiloxane on silicon dioxide, and wherein the cosmetic agent contains a divalent and/or or trivalent alcohol, which is preferably selected from the group consisting of ethylene glycol, 1,2-propylene glycol, 2-methyl-1,3-propanediol, glycerol, 1,2-butylene glycol, 1,3-butylene glycol, 1,4-butylene glycol, 1,2-pentanediol, and 1,5-pentanediol, and in particular glycerol.

H)
Cosmetic agent for treating keratinic fibers, in particular human hair, wherein the cosmetic agent constitutes a powder comprising hydrophobically modified silicon dioxide and particles comprising a composite material, wherein the composite material comprises a crosslinked polyorganosiloxane on silicon dioxide, and wherein the hydrophobically modified silicon dioxide is a silylation product of a reaction of a precipitated silica and/or a fumed silica with an organosilicon compound.

I)
Cosmetic agent for treating keratinic fibers, in particular human hair, wherein the cosmetic agent constitutes a powder comprising hydrophobically modified silicon dioxide and particles comprising a composite material, wherein the composite material comprises a crosslinked polyorganosiloxane on silicon dioxide, and wherein the hydrophobically modified silicon dioxide is a silylation product of a reaction of a precipitated silica and/or a fumed silica with an alkylsilazane, in particular hexamethyldisilazane.

J)
Cosmetic agent for treating keratinic fibers, in particular human hair, wherein the cosmetic agent constitutes a powder comprising hydrophobically modified silicon dioxide and particles comprising a composite material, wherein the composite material comprises a crosslinked polyorganosiloxane on silicon dioxide, wherein the cosmetic agent contains from about 50 to about 90% by weight, preferably from about 60 to about 95% by weight, more preferably from about 70 to about 80% by weight of water, from about 5 to 30% by weight, preferably from about 6 to about 25% by weight, more preferably from about 7 to about 20% by weight of hydrophobically modified silicon dioxide, and from about 2 to about 30% by weight, preferably from about 5 to about 25% by weight, more preferably from about 7 to about 20% by weight of composite material, each based on the total weight of the cosmetic agent.

The object underlying the present disclosure is further achieved by a spray applicator. A second subject of the present disclosure is therefore a spray applicator comprising a cosmetic agent according to the first aspect of the present disclosure. The spray applicator is preferably a pump sprayer. Alternatively, the present disclosure relates to a spray applicator containing a cosmetic agent which, according to a preferred embodiment, does not comprise a propellant.

Spray applicators such as so-called powder spray dispensers are known in the art. For example, EP 0473965 A1 discloses a discharge device for media, which should be suitable in particular for a single medium, identical or dissimilar flowable media of possibly different state of matter that are separately stored, wherein the medium can preferably be at least partially free-flowing, for example, powder and/or or powdery.

Spray applicators particularly preferred as contemplated herein relate to the following embodiments:

According to one aspect of the particularly preferred spray applicators, the spray applicator comprises a cosmetic agent for treating keratinic fibers, in particular human hair, wherein the cosmetic agent constitutes a powder containing hydrophobically modified silicon dioxide and particles comprising a silicone elastomer.

A further embodiment relates to a spray applicator according to the preceding aspect, wherein the silicone elastomer is a crosslinked polyorganosiloxane selected from the group consisting of a crosslinked polydimethylsiloxane, a crosslinked polydimethylsiloxane/methylvinylsiloxane, a crosslinked poly dimethylsiloxane/diphenylsiloxane, a crosslinked polydimethylsiloxane/phenylmethylsiloxane, a crosslinked polydimethylsiloxane/diphenylsiloxane/methylvinylsiloxane, a polydimethylsiloxane gum and a crosslinked Dimethiconol (INCI).

A further embodiment relates to a spray applicator according to the preceding aspects, wherein the particles comprising a silicone elastomer constitute a composite material, wherein the composite material comprises a crosslinked polyorganosiloxane and silicon dioxide, preferably wherein the composite material comprises a crosslinked polyorganosiloxane on silicon dioxide, more preferably wherein the composite material comprises Dimethicone/Vinyldimethicone Crosspolymer (INCI) on silicon dioxide, and most preferably wherein the composite material consists of Dimethicone/Vinyldimethicone Crosspolymer (INCI) and silicon dioxide.

A further embodiment relates to a spray applicator according to the preceding aspects, wherein the particles, in particular the composite material, have an average particle size of from about 0.1 to about 20 µm, preferably from about 0.5 to about 15 µm, more preferably from about 0.9 to about 12 µm and most preferably from about 1 to about 10 µm.

A further embodiment relates to a spray applicator according to the preceding aspects, wherein the cosmetic agent contains an organic acid, preferably a divalent and/or trivalent organic acid, more preferably a divalent and/or trivalent carboxylic acid, most preferably citric acid.

A further embodiment relates to a spray applicator according to the preceding aspects, wherein the hydrophobically modified silicon dioxide is a silylation product of a reaction of a precipitated silica and/or a fumed silica with an organosilicon compound, wherein the organosilicon compound is preferably an alkylsiloxane, a silane, preferably trimethylsilane, or a silazane, wherein more preferably the organosilicon compound is an alkylsilazane, in particular hexamethyldisilazane.

A further embodiment relates to a spray applicator according to the preceding aspects, wherein the cosmetic agent contains a) from about 50 to about 90% by weight, preferably from about 60 to about 95% by weight, more preferably from about 70 to about 80% by weight of water, b) from about 5 to about 30% by weight, preferably from about 6 to about 25% by weight, more preferably from about 7 to about 20% by weight of hydrophobically modified silicon dioxide, and c) from about 2 to about 30% by weight, preferably from about 5 to about 25% by weight, more preferably from about 7 to about 20% by weight of particles comprising the silicone elastomer, in each case based on the total weight of the cosmetic agent.

A further embodiment relates to a spray applicator according to the preceding aspects, wherein the cosmetic agent further comprises a water-soluble care agent, which is preferably a polyvalent alcohol, which is more preferably selected from the group consisting of ethylene glycol, 1,2-propylene glycol, 2-methyl-1,3-propanediol, glycerol, 1,2-butylene glycol, 1,3-butylene glycol, 1,4-butylene glycol, 1,2-pentanediol, 1,5-pentanediol, in particular glycerol, and/or exemplified in that the cosmetic agent further contains a water-soluble care agent, in particular glycerol, in an amount of from about 2 to about 18% by weight, preferably from about 5 to about 15% by weight, more preferably from about 8 to about 12% by weight, based on the total weight of the cosmetic agent.

A particularly preferred embodiment of the present disclosure comprises a spray applicator containing a cosmetic agent for treating keratinic fibers, in particular human hair, wherein the cosmetic agent constitutes a powder comprising hydrophobically modified silicon dioxide and particles comprising a composite material, wherein the composite material comprises a crosslinked polyorganosiloxane on silicon dioxide wherein the cosmetic agent contains from about 50 to about 90% by weight, preferably from about 60 to about 95% by weight, more preferably from about 70 to about 80% by weight of water, from about 5 to about 30% by weight, preferably from about 6 to about 25% by weight, more preferably from about 7 to about 20% by weight of hydrophobically modified silicon dioxide, and from about 2 to about 30% by weight, preferably from about 5 to about 25% by weight, more preferably from about 7 to about 20% by weight of composite material, each based on the total weight of the cosmetic agent.

A third subject of the present disclosure relates to the use of the cosmetic agent according to the first subject of the present disclosure for the care of keratinic fibers, in particular human hair, for shaping keratinic fibers, in particular human hair, for giving volume to a hairstyle of human hair, and/or styling a hairstyle from human hair.

Features relating to preferred embodiments of the first subject of the present disclosure, which are described above only in this regard, of course, apply mutatis mutandis to the second and third subjects as features of preferred embodiments.

The following examples are intended to illustrate the subject matter of the present disclosure without limiting it in any way.

EXAMPLES

Cosmetic compositions as contemplated herein were prepared according to the following formulations:

|  | E1* | E2* | E3* |
|---|---|---|---|
| Demineralized water | 74.48 | 74.48 | 74.48 |
| Glycerol 99.5% | 10.0 | 10.0 | 10.0 |
| Citric acid Monohydrate Regular | 0.12 | 0.12 | 0.12 |
| Sodium benzoate | 0.4 | 0.4 | 0.4 |
| Aerosil R 812 S | 7.5 | 9 | 11 |
| Dow Corning 9701 Cosmetic Powder | 7.5 | 6 | 4 |

*specification in % by weight

The cosmetic compositions E1, E2 and E3 are prepared by mixing the components. The compositions can be taken and massaged into the hair. The hair is then brought into the desired shape.

While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration of the various embodiments in any way. Rather, the foregoing detailed description will provide those skilled in the art with a convenient road map for implementing an exemplary embodiment as contemplated herein. It being understood that various changes may be made in the function and arrangement of elements described in an exemplary embodiment without departing from the scope of the various embodiments as set forth in the appended claims.

The invention claimed is:

1. A cosmetic agent for treating keratinic fibers comprising 50-90% by weight water, from 5 to 30% by weight of a hydrophobically modified silicon dioxide, and 2 to 30% by weight particles comprising a silicone elastomer, each based on the total weight of the cosmetic agent.

2. The cosmetic agent according to claim 1, wherein the silicone elastomer is a crosslinked polyorganosiloxane selected from the group of a crosslinked polydimethylsiloxane, a crosslinked polydimethylsiloxane/methylvinylsiloxane, a crosslinked polydimethylsiloxane/diphenylsiloxane, a crosslinked polydimethylsiloxane/phenylmethylsiloxane, a crosslinked polydimethylsiloxane/diphenylsiloxane/methylvinylsiloxane, a polydimethylsiloxane gum and a crosslinked Dimethiconol.

3. The cosmetic agent according to claim 1, wherein the particles comprising a silicone elastomer include a composite material, wherein the composite material comprises a crosslinked polyorganosiloxane and silicon dioxide.

4. The cosmetic agent according to claim 3, wherein the composite material comprises a crosslinked polyorganosiloxane on silicon dioxide.

5. The cosmetic agent according to claim 3, wherein the composite material comprises Dimethicone/Vinyldimethicone Crosspolymer (INCI) on silicon dioxide.

6. The cosmetic agent according to claim 1, wherein the composite material consists of Dimethicone/Vinyldimethicone Crosspolymer and silicon dioxide.

7. The cosmetic agent according to claim 1, wherein the particles have an average particle size of from about 0.1 to about 20 μm.

8. The cosmetic agent according to claim 1, wherein the cosmetic agent comprises a divalent carboxylic acid or a trivalent carboxylic acid.

9. The cosmetic agent according to claim 1, wherein the hydrophobically modified silicon dioxide is a silylation product of a reaction of a precipitated silica and/or a fumed silica with an organosilicon compound.

10. The cosmetic agent according to claim 1, wherein the hydrophobically modified silicon dioxide is a silylation product of a reaction of a precipitated silica and/or a fumed silica with an alkylsiloxane, a silane, or a silazane.

11. The cosmetic agent according to claim 1, wherein the hydrophobically modified silicon dioxide is a silylation product of a reaction of a precipitated silica and/or a fumed silica with trimethylsilane or hexamethyldisilazane.

12. The cosmetic agent according to claim 1, wherein the cosmetic agent comprises:
a) from about 70 to about 80% by weight of water,
b) from about 7 to about 20% by weight of the hydrophobically modified silicon dioxide, and
c) from about 7 to about 20% by weight of the particles comprising the silicone elastomer,
each based on the total weight of the cosmetic agent.

13. The cosmetic agent according to claim 1, wherein the cosmetic agent further comprises a water-soluble care agent.

14. The cosmetic agent according to claim 13 wherein the water-soluble care agent is selected from the group consisting of ethylene glycol, 1,2-propylene glycol, 2-methyl-1,3-propanediol, glycerol, 1,2-butylene glycol, 1,3-butylene glycol, 1,4-butylene glycol, 1,2-pentanediol, and 1,5-pentanediol.

15. The cosmetic agent according to claim 14, wherein the water-soluble care agent is present in an amount of from about 2 to about 18% by weight, based on the total weight of the cosmetic agent.

16. A spray applicator comprising a cosmetic agent according to claim 1.

17. The cosmetic agent according to claim 1, comprising:
from about 70 to about 80% by weight of water from about 7 to about 20% by weight of hydrophobically modified silicon dioxide that is a silylation product of a reaction of a precipitated silica and/or a fumed silica with an organosilicon compound;
from about 7 to about 20% by weight of particles comprising a composite material, wherein the composite material consists of Dimethicone/Vinyldimethicone Crosspolymer and silicon dioxide;
a divalent carboxylic acid or a trivalent carboxylic acid; and
from about 2 to about 18% by weight of a water-soluble care agent selected from the group consisting of ethylene glycol, 1,2-propylene glycol, 2-methyl-1,3-propanediol, glycerol, 1,2-butylene glycol, 1,3-butylene glycol, 1,4-butylene glycol, 1,2-pentanediol, and 1,5-pentanediol;
wherein the particles have an average particle size of from about 0.1 to about 20 μm;
each based on the total weight of the cosmetic agent.

* * * * *